(12) United States Patent
Wöhrle et al.

(10) Patent No.: US 6,916,966 B2
(45) Date of Patent: Jul. 12, 2005

(54) PROCESS FOR PREPARING CYCLOALKADIENES

(75) Inventors: Ingo Wöhrle, Holzminden (DE); Peter Esser, Summerville, SC (US); Aurélia Reckziegel, Holzminden (DE); Matthias Brandt, Düsseldorf (DE); Stephan Klein, Bergisch Gladbach (DE); Thomas Turek, Düsseldorf (DE)

(73) Assignee: Symrise GmbH & Co. KG, Holzminden (DE)

( * ) Notice: Subject to any disclaimer, the term of this patent is extended or adjusted under 35 U.S.C. 154(b) by 338 days.

(21) Appl. No.: 10/227,649

(22) Filed: Aug. 23, 2002

(65) Prior Publication Data

US 2003/0069460 A1 Apr. 10, 2003

(30) Foreign Application Priority Data

Aug. 28, 2001 (DE) .......................... 101 42 032

(51) Int. Cl.⁷ .............................. C07C 6/00; C07C 6/06
(52) U.S. Cl. ........................ 585/646; 585/647; 585/353; 585/354
(58) Field of Search ................................ 585/646, 647, 585/353, 354

(56) References Cited

U.S. PATENT DOCUMENTS

| 4,668,836 A |   | 5/1987  | Eberle et al. ............... 585/364 |
| 4,684,760 A | * | 8/1987  | Drake ........................ 585/670 |
| 4,754,098 A | * | 6/1988  | Drake ........................ 585/646 |
| 4,889,840 A | * | 12/1989 | Drake ........................ 502/255 |
| 5,898,092 A | * | 4/1999  | Commereuc ................ 585/647 |
| 2003/0069460 A1 | * | 4/2003 | Wohrie et al. ............. 585/646 |
| 2003/0230598 A1 | * | 12/2003 | Kendall et al. ........... 222/145.6 |

FOREIGN PATENT DOCUMENTS

| CA | 1325642 | 12/1993 |
| EP | 0 991 467 | 5/2001 |

OTHER PUBLICATIONS

Chemiker–Zeitung 107, (month unavailable) 1983, pp. 115–120, Von Siegfried Warwel, Heinz Ridder und Gerd Hachen, "Olefinsynthesen durch Metathese".

* cited by examiner

*Primary Examiner*—Elizabeth D. Wood
(74) *Attorney, Agent, or Firm*—Pendorf & Cutliff

(57) ABSTRACT

The present invention relates to a process for preparing cycloalkadienes using supported catalysts based on $Re_2O_7/\gamma\text{-}Al_2O_3$ and also to the use of the resulting cycloalkadienes for the preparation of fragrances.

4 Claims, 1 Drawing Sheet

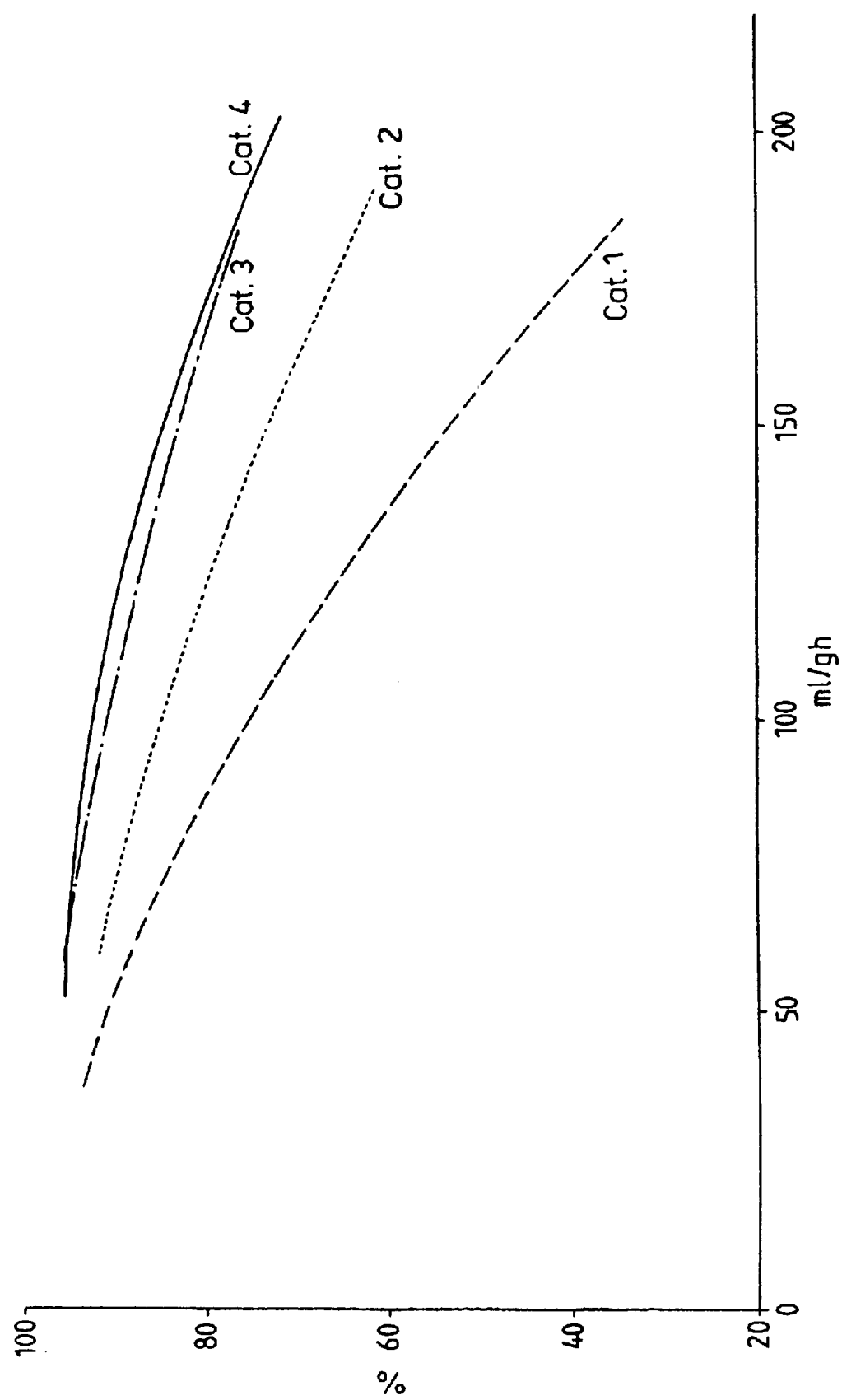

PROCESS FOR PREPARING CYCLOALKADIENES

FIELD OF THE INVENTION

The present invention relates to a process for preparing cycloalkadienes using supported catalysts based on $Re_2O_7/\gamma\text{-}Al_2O_3$ and also to the use of the cycloalkadienes produced.

Cycloalkenes, preferably cycloalkadienes having a ring size of from 12 to 18 carbon atoms, are used, inter alia, for preparing oxygen-containing, macrocyclic compounds. The compounds can be used in the preparation of macrocyclic ketones, lactones and epoxides that are useful as musk fragrances in the perfume industry.

BACKGROUND OF THE INVENTION

EP-A 182 333 discloses that highly dilute cycloolefin solutions can be converted by a metathesis reaction in the liquid phase using the catalyst system $Re_2O_7/\gamma\text{-}Al_2O_3/SnR_4$, where R is an alkyl radical, into the corresponding cycloalkadienes.

The preparation of cycloalkadienes by a metathesis reaction of cyclooctenylenes having a degree of polymerization of greater than or equal to three and/or cycloalkamonoenes in the liquid phase in the presence of a supported catalyst based on $Re_2O_7/\gamma\text{-}Al_2O_3$ is described in EP-A 343 437.

Chemiker-Zeitung 1983, 107, 115, describes the preparation of cycloalkadienes over a $Re_2O_7/\gamma\text{-}Al_2O_3$ catalyst. As support material, use was made of $\gamma\text{-}Al_2O_3$-CK-300 from Akzo.

EP-B 991 467 describes $Re_2O_7/\gamma\text{-}Al_2O_3$ catalysts containing boron oxide and having the form of extrudates.

Due to the necessarily high dilution of the cycloolefin solutions used in the metathesis reaction, the amount of cycloalkadienes, which is obtainable per unit time, has been unsatisfactory from economic, engineering and industrial points of view.

SUMMARY OF THE INVENTION

It is an object of the present invention to provide supported catalysts and processes by means of which a larger amount of cycloalkadienes can be prepared per unit time.

It is also an object of the present invention to achieve a higher productivity and a higher space-time yield during the metathesis process.

It has now surprisingly been found that supported catalysts having a high specific external surface area can provide a significant increase in the activity and productivity of the supported $Re_2O_7/\gamma\text{-}Al_2O_3$ catalyst. This is particularly noticeable at relatively high space velocities, so that the amount of cycloalkadienes prepared per unit time can be significantly increased. Furthermore, it has been found that more metathesis products and cycloalkadienes can be prepared within a supported catalyst cycle.

Accordingly, the present invention provides a process for preparing cycloalkadienes from cycloalkamonoenes, cyclopolyenes, acyclic polyenes or mixtures thereof by a metathesis reaction in the liquid phase in the presence of a shaped supported catalyst body based on $Re_2O_7/\gamma\text{-}Al_2O_3$, characterized in that the calculated specific external surface area of the shaped supported catalyst body is greater than or equal to 3.5 $mm^2/mm^3$.

The present invention further provides for the use of the cycloalkadienes prepared by the process of the present invention for the preparation of fragrances, preferably for the preparation of macrocyclic fragrances.

BRIEF DESCRIPTION OF THE DRAWINGS

The FIGURE illustrates, in graph form, the cyclooctene-based conversion (in percent, x axis) as a function of the space velocity (in ml/gh, y axis) in a metathesis reaction using the supported catalysts of the invention (Cat. 2 to 4) in comparison with a commercially available supported catalyst Cat. 1.

DETAILED DESCRIPTION OF THE INVENTION

For the purposes of the present invention, a metathesis solution is the starting solution, i.e. a solvent containing at least one hydrocarbon selected from the group consisting of cycloalkamonoenes, cyclopolyenes and acyclic polyenes.

The supported catalysts of the present invention display a significantly higher activity, as a result of which a higher space-time yield and a higher productivity for cycloalkadienes can be achieved. The supported catalysts are described in more detail in Table 2 and Example 1, and the experimental conditions are described in more detail in Example 2.

For the purposes of the present invention, the specific external surface area is the ratio of the calculated, geometric external surface area to the calculated total geometric volume of the shaped supported catalyst body.

Suitable supported catalysts have a specific external surface area of greater than or equal to 3.5 $mm^2/mm^3$, preferably one of greater than or equal to 4.0 $mm^2/mm^3$, more preferably one of greater than or equal to 5.0 $mm^2/mm^3$.

The supported catalysts are used as shaped bodies of any shape, for example hollow rods, extrudates, ram extrudates, spheres, hollow cylinders, cylinders, cubes, cones and the like. Preference is given to spheres, swirl strands (SS) or cylinders.

The bulk density of the supported catalysts is typically in the range from 400 to 900 g/l.

The supported catalysts typically have specific surface areas of from 100 to 300 $m^2/g$ determined by the BET method (Brunauer, Emmett and Teller method).

To illustrate the determination of the specific external surface area of the supported catalyst in shaped bodies, a few non-limiting examples are given in Table 1.

TABLE 1

Calculation of the specific external surface area

|  | Sphere | Sphere | Cylinder | Hollow cylinder |
|---|---|---|---|---|
| External Diameter (mm) | 1.0 | 1.5 | 0.8 | 3.5 |
| Internal Diameter (mm) | — | — | — | 2 |
| Length (mm) | — | — | 6 | 4 |
| Volume ($mm^3$) | 0.52 | 1.77 | 3.02 | 38.5 |
| External Surface Area ($mm^2$) | 3.14 | 7.07 | 16.09 | 82.1 |
| Specific | 6.00 | 4.00 | 5.33 | 2.13 |

TABLE 1-continued

Calculation of the specific external surface area

|  | Sphere | Sphere | Cylinder | Hollow cylinder |
|---|---|---|---|---|
| External Surface Area ($mm^2/mm^3$) | | | | |

Preference is given to a continuous reaction procedure, preferably a vertical arrangement of the supported catalysts in a fixed bed, with the metathesis solution preferably being passed through the fixed bed from the bottom upwards.

The $Re_2O_7$ content of the supported catalyst, based on the weight of the supported catalyst, is preferably in the range from 1 to 12% by weight, more preferably in the range from 2 to 8% by weight, most preferably in the range from 3 to 6% by weight. The supported catalysts are prepared by methods known to those skilled in the art. The rhenium is usually applied by impregnation of the support material with an aqueous solution of one or more rhenium compounds and subsequent thermal treatment of the material, resulting in formation of $Re_2O_7$. Suitable rhenium compounds include, for example, perrhenates such as ammonium perrhenate, but it is also possible to use perrhenic acid or rhenium heptoxide itself. Thermal treatment of the supported catalyst is carried out in a temperature range from 200 to 600° C., with the maximum useable temperature being in the region of about 600° C.

It is preferably for the supported catalyst to contain from 0.5 to 40% by weight, preferably from 1 to 20% by weight, more preferably from 1 to 10% by weight, of a tin tetraalkyl or tin dioxide or a mixture of these tin compounds. Preferred tin tetraalkyls include tetramethyltin, tetraethyltin, tetra-n-butyltin, tetra-n-octyltin; most preferred is tetramethyltin. It is preferable for the supported catalyst to be brought into contact with a solution containing a tin tetraalkyl before commencement of the metathesis reaction, in which case it is also possible to use mixtures of the above mentioned tin tetraalkyls. Application of tin dioxide can be carried out, for example, in the regeneration of the supported catalyst containing a tin tetraalkyl, but can also be achieved by impregnating the supported catalyst with water-soluble tin compounds and subsequently heating it to 500–600° C. in an oxygen-containing atmosphere, resulting in formation of tin oxide.

Furthermore, it is advantageous for the metathesis reaction to be carried out in the presence of a tin tetraalkyl. The tin tetraalkyls are typically added to the metathesis solution before commencement of the metathesis reaction, and this mixture is conveyed from a reservoir over the bed of supported catalyst. The tin tetraalkyls are typically added to the metathesis solution in an amount of from 0.1 to 8% by weight, preferably from 0.1 to 5% by weight, more preferably from 0.1 to 2.5% by weight, based on the weight of the supported catalyst. Preferred tin tetraalkyls include tetramethyltin, tetraethyltin, tetra-n-butyltin, tetra-n-octyltin; more preferred is tetramethyltin.

It is preferable to treat the supported catalyst with one or more mineral acids, in which case the treatment can be carried out before or after application of the rhenium. Preference is given to treating the $\gamma$-$Al_2O_3$ support material or the Re-laden supported catalyst with an aqueous HCl solution.

Preferably the supported catalysts contain from 0.2 to 3% by weight of cesium, in which case treatment with one or more cesium compounds can be carried out before or after application of the rhenium. Preference is given to treatment with an aqueous cesium nitrate solution.

Also advantageous are supported catalysts containing from 0.3 to 3% by weight of phosphorus, in which case treatment with one or more phosphorus compounds can be carried out before or after application of the rhenium. Preference is given to treatment with an aqueous ammonium phosphate solution, particularly and preferably with diammonium hydrogen phosphate.

The above mentioned dopants, active ingredients or treatments are preferably applied to the supported catalyst by means of impregnation, but it is also possible to produce the supported catalysts by means of digestion.

The content of cycloalkamonoenes, cyclopolyenes, acyclic polyenes or mixtures thereof in the liquid phase is typically in the range from 0.5 to 10 g/l, preferably in the range from 1.0 to 5.5 g/l, more preferably in the range from 2.0 to 4.0 g/l.

The starting materials are used in metathesis-inert solvents. Suitable solvents include, for example, hydrocarbons and halogenated hydrocarbons, such as butane, pentane, hexane, heptane, octane, cyclopentane, cyclohexane, cyclooctane, dichloromethane and trichloroethane. Preference is given to n-pentane, n-hexane, n-heptane, n-octane, iso-octane, cyclopentane and cyclohexane; more preference is given to n-pentane and n-hexane. It is also possible to use mixtures of hydrocarbons, e.g. petroleum ether.

Preferable cycloalkamonoenes include those having a ring size of from 4 to 12 carbon atoms. Preferred cycloalkamonoenes include cyclopentene, cyclohexene, cycloheptene, cyclooctene, cyclononene, cyclodecene and cyclododecene. More preference is given to cycloheptene and cyclooctene.

Useful cyclopolyenes or acyclic polyenes include those, which can be obtained from the cycloalkamonoenes mentioned. The cyclopolyenes or acyclic polyenes can, for example, be formed as by-products in metathetic dimerizations, by ring-opening metatheses or polymerizations. In general, the cyclopolyenes and the acyclic polyenes have a degree of polymerization of from 3 to 50, preferably one of from 3 to 20. For the purposes of the present invention, the degree of polymerization is the number of monomer units, identical or different, of which the polyene is built up.

According to the present invention, preferred cyclopolyenes include polymers and copolymers of the cycloalkamonoenes mentioned, with the cyclopolyenes having a degree of polymerization of greater than or equal to three, preferably from 3 to 50, more preferably from 3 to 20. Preference is given to using cyclopolyenes derived from cycloheptene, cyclooctene or their copolymers.

More preferred cyclopolyenes include cyclopolyocteneylenes of the formula:

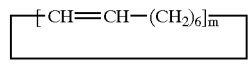

having a degree of polymerization, m, of at least 3, wherein m is preferably in the range from 3 to 50, more preferably in the range from 3 to 20.

Cycloalkamonoenes, cyclopolyenes and acyclic polyenes can be present in the metathesis solutions in any compositions and mixing ratios. Preference is given to metathesis solutions containing cycloalkamonoenes. If metathesis solutions containing only cycloalkamonoenes as olefinic compounds are used, preference is given to cycloheptene, cyclooctene or mixtures thereof. Preference is also given to mixtures of cycloalkamonoenes and cyclopolyenes, with mixtures containing cycloheptene, cyclooctene or a mixture thereof and cyclopolyheptenylene, cyclopolyoctenylene, copolymers of cycloheptene and cyclooctene or a mixture thereof being more preferred.

If mixtures of cycloalkamonoenes and cyclopolyenes are used, the preferred weight ratio is in the range 0.1–2:1, more preferably in the range 0.2–1:1.

Preference is given to a mixture of cyclooctene and cyclopolyoctenylene, in which case a ratio of cyclooctene to cyclopolyoctenylenes in the range 0.25–0.5:1 is most preferred.

If cycloalkamonoenes or mixtures containing cycloalkamonoenes are used in the metathesis reaction, it is preferable to set a conversion, based on the content of cycloalkamonoenes, in the range from 40 to 99%, preferably in the range from 50 to 95%, more preferably in the range from 60 to 85%.

The metathesis solution can also contain small proportions of cycloalkadienes, preferably the cycloalkadienes to be formed, i.e. product cycloalkadienes. These can be present in small amounts in the cycloalkamonoenes, cyclopolyenes or the acyclic polyenes and result from, for example, distillation.

Preferred cycloalkadienes, which can be prepared by the process of the present invention, include those having from 12 to 18 carbon atoms. More preferred cycloalkadienes include 1,8-cyclotetradecadiene, 1,8-cyclopentadecadiene and 1,9-cyclohexadecadiene. Most preference is given to 1,9-cyclohexadecadiene.

The metathesis reaction can be carried out at temperatures in the range from 0 to 100° C., preferably at a temperature in the range from 25 to 80° C., more preferably in the range from 35 to 60° C.

If solvents having boiling points below the reaction temperature are used, the reaction can also be carried out under atmospheric pressure. In general, the metathesis reaction can be carried out at a pressure in the range from 1 to 10 bar abs.

After use in the metathesis reaction, the supported catalyst can be regenerated and reused for the metathesis reaction. As described, for example, in EP-B1-991 467, the supported catalyst can be removed from the metathesis reactor, washed with a metathesis-inert solvent and subsequently dried. Thermal treatment of the supported catalyst in the regeneration is carried out in a temperature range from 200 to 600° C., with the maximum useable temperature being about 600° C. Thermal treatment is carried out in an oxygen-containing atmosphere, for example air which can, if desired, be additionally admixed with inert gases such as nitrogen or argon.

EXAMPLES

The following examples illustrate the invention:

Example 1

The support materials comprising γ-aluminum oxide were obtained commercially (e.g. from Condea, from KataLeuna). If necessary, individual particle fractions were obtained by screening procedures.

The γ-aluminum oxide (240 g) as the respective shaped bodies was impregnated with an aqueous solution of ammonium perrhenate (16.5 g in 240 ml of distilled water) and dried. After treatment at 500–580° C. in a stream of air for 2 hours, the catalyst was kept at the same temperature in a stream of nitrogen for a further 2 hours and subsequently cooled to room temperature. The physical characteristics are shown in Table 2.

TABLE 2

| | $Re_2O_7$-containing supported catalysts | | | |
|---|---|---|---|---|
| Shape | Cat. 1 Cylinder | Cat. 2 Sphere | Cat. 3 Sphere | Cat. 4 Cylinder |
| External Diameter (mm) | 1.7 | 1.5 | 1.0 | 0.8 |
| Length (mm) | 10 | — | — | 8 |
| Specific External Surface Area $(mm^2/mm^3)$ | 2.55 | 4.00 | 6.00 | 5.25 |
| BET Surface Area $(m^2/g)$ | 208 | 216 | 163 | 199 |

The $Re_2O_7$ content of all the supported catalysts shown in Table 2 was from 3.6 to 3.7% by weight, and the γ-$Al_2O_3$ content was from 95.8 to 96.0% by weight.

The catalysts in Table 2 were tested under the conditions described in Example 2 and compared with the commercially available Cat. 1 (cylindrical extrudates, support material: γ-$Al_2O_3$-CK-300 from Akzo) (see the FIGURE).

Example 2

50 g of one of the supported catalysts shown in Table 2 were in each case placed in a vertical tube reactor (height: 50 cm, diameter: 1.5 cm) under a protective gas atmosphere (argon). A solution of 2.5% by weight of tetramethyltin (based on the weight of the supported catalyst) in n-hexane was circulated by means of a pump through the fixed bed of the supported catalyst from bottom upwards at 30° C. for 3 hours. A solution containing 2.4 g of cyclooctene and 0.5% by weight of tetramethyltin (based on the weight of the supported catalyst) per liter of n-hexane was then passed continuously through the bed of supported catalyst from the bottom upwards at 45° C. and atmospheric pressure.

The amount of metathesis solution passed over the bed of supported catalyst per unit time, i.e. the space velocity, was varied by means of the pump output.

The selectivity to 1,9-cyclohexadecadiene over the entire reaction time was from 36 to 38%. The selectivity to 1,9-cyclohexadecadiene and cyclopolyoctenylenes was 99%.

The FIGURE, in graph form, the cyclooctene-based conversion (in percent, x-axis) as a function of the space velocity (in ml/gh, y-axis) in a metathesis reaction using the supported catalysts of the invention (Cat. 2 to 4) in comparison with the commercially available supported catalyst Cat. 1. The supported catalysts of the invention display a significantly higher activity.

Example 3

γ-Aluminum oxide (240 g) in the form of 1.0 mm spheres (obtainable from Condea) was impregnated with a solution of rhenium oxide (9 g in 120 g of distilled water) and subsequently dried. After treatment at 500–580° C. in a stream of air for 2 hours, the catalyst was kept at the same temperature in a stream of nitrogen for a further 2 hours and subsequently cooled to room temperature. After impregnation with an aqueous cesium nitrate solution (1.8 g of cesium nitrate in 125 ml of distilled water), the catalyst was dried at 120° C. for two hours, followed by treatment at 500° C. in a stream of air for two hours and cooling in a stream of nitrogen. This gave a supported catalyst in the form of 1.0 mm spheres which contained 3.6% by weight of $Re_2O_7$ and 0.5% by weight of cesium.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a cycloalkadiene by a metathesis reaction comprising the step of reacting a cycloalkamonoene, a cyclopolyene, an acyclic polyene or mixtures thereof in the liquid phase, in the presence of a shaped supported catalyst body comprising $Re_2O_7/\gamma\text{-}Al_2O_3$, wherein the calculated specific external surface area of the shaped supported catalyst body is greater than or equal to 3.5 $mm^2/mm^3$.

2. The process according to claim 1, wherein the calculated specific surface area of the shaped supported catalyst body is greater than or equal to 4.0 $mm^2/mm^3$.

3. The process according to claim 1, wherein the shaped body is a sphere, a cylinder or a swirl strand.

4. The process according to claim 1, wherein the supported catalyst has an $Re_2O_7$ content in the range from 1 to 12% by weight.

* * * * *